(12) United States Patent
Matheny

(10) Patent No.: US 8,758,448 B2
(45) Date of Patent: Jun. 24, 2014

(54) LAMINATE SHEET ARTICLES FOR TISSUE REGENERATION

(75) Inventor: Robert G. Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 175 days.

(21) Appl. No.: 13/033,102

(22) Filed: Feb. 23, 2011

(65) Prior Publication Data

US 2012/0016491 A1     Jan. 19, 2012

Related U.S. Application Data

(63) Continuation of application No. 12/394,914, filed on Feb. 27, 2009, now abandoned, which is a continuation of application No. 11/747,004, filed on May 10, 2007, now abandoned.

(51) Int. Cl.
    *A61F 2/02*     (2006.01)
    *A61K 35/12*     (2006.01)
    *A61L 27/36*     (2006.01)
    *A61L 27/38*     (2006.01)

(52) U.S. Cl.
    CPC .......... *A61L 27/3633* (2013.01); *A61L 27/3629* (2013.01); *A61L 27/3679* (2013.01); *A61L 27/3804* (2013.01); *A61K 35/12* (2013.01)
    USPC .......................... 623/23.72; 424/443; 424/572

(58) Field of Classification Search
    CPC   A61K 35/12; A61L 27/3629; A61L 27/3633; A61L 27/2679; A61L 27/3804
    USPC ....................................................... 623/23.72
    See application file for complete search history.

(56) References Cited

U.S. PATENT DOCUMENTS

| | | | |
|---|---|---|---|
| 6,379,710 B1 * | 4/2002 | Badylak | 424/553 |
| 6,497,875 B1 * | 12/2002 | Sorrell et al. | 424/93.7 |
| 2005/0222661 A1 * | 10/2005 | Case et al. | |
| 2006/0147433 A1 * | 7/2006 | Hiles | |
| 2010/0233235 A1 | 9/2010 | Matheny et al. | |

FOREIGN PATENT DOCUMENTS

WO    WO 2012/018680    2/2012

OTHER PUBLICATIONS

Nerem, R., 2006, Tissue Engineering, vol. 12, No. 5, p. 1143-1150.*

* cited by examiner

*Primary Examiner* — Shin Lin Chen
(74) *Attorney, Agent, or Firm* — Francis Law Group

(57) ABSTRACT

The invention is to articles of extracellular matrix. The articles comprise one or more sheets of mammalian extracellular matrix laminated together. A single sheet can be folded over and laminated on 3 sides. Two or more sheets can be laminated to each other at their edges. The sheets can further encase a composition comprising a cell or cells, such as for example, a stem cell. A single sheet can be folded over to encase a composition, or rolled to encase a composition with lamination at either end of the roll, for example. The invention also includes methods of using these articles to regenerate tissue at tissue defects, or heal wounds in damaged tissue.

4 Claims, 3 Drawing Sheets

LAMINATE SHEET ARTICLES FOR TISSUE REGENERATION

CROSS-REFERENCE TO RELATED APPLICATIONS

This application is a continuation of U.S. patent application Ser. No. 12/394,914, filed Feb. 27, 2009 now abandoned, which is a continuation of U.S. patent application Ser. No. 11/747,004, filed May 10, 2007, now abandoned, which applications are hereby incorporated herein by reference in their entireties.

FIELD OF THE INVENTION

The invention relates to articles and compositions having two or more forms of extracellular matrix.

BACKGROUND OF THE INVENTION

Tissue regeneration has been accomplished by using extracellular matrix material derived from mammalian tissues. Some of these mammalian tissues that have been described in patent literature include small intestine submucosa (SIS), liver basement membrane (LBM), urinary bladder submucosa (UBS) and stomach submucosa (SS). See U.S. Pat. Nos. 5,554,389, 4,902,508, and 5,281,422. Enamel matrices, which are the extracellular matrix around forming teeth, are described in U.S. Pat. No. 7,033,611. Extracellular matrices from these tissues have been isolated and dried to become solid materials (sheets and particulates). Particulate forms can be rehydrated in a suitable buffer to become fluidized or emulsive forms. Presently, these extracellular matrix compositions are used for tissue grafting, wound healing, and tissue regenerative purposes. (cite WSJ article)

It would be advantageous to the field of tissue engineering to invent articles and compositions for effecting improved tissue regeneration.

SUMMARY OF THE INVENTION

The invention is an article for wound healing and tissue regeneration comprising two or more sheets of mammalian extracellular matrix, said sheets of mammalian extracellular matrix laminated to each other to form a planar laminated article of mammalian extracellular matrix.

The invention is an article for wound healing and tissue regeneration comprising two or more sheets of mammalian extracellular matrix, said sheets of mammalian extracellular matrix laminated to each other to form a planar laminated article of mammalian extracellular matrix, said article further comprising in between at least two of said sheets at least one cell to further effect wound healing or tissue regeneration upon placement of said laminated article in a mammal at a site in said mammal in need of wound healing or tissue regeneration.

In the article the cell can be a stem cell. The cell can be a mesechymal cell.

The invention is also a method comprising: identifying a defect or wound in mammalian tissue which could benefit from tissue regeneration or wound healing, providing an article comprising two or more sheets of mammalian extracellular matrix, said sheets of mammalian extracellular matrix laminated to each other to form a planar laminated article of mammalian extracellular matrix, contacting said defect or wound with said article, and regenerating tissue at said defect or healing said wound thereby.

DETAILED DESCRIPTION OF THE INVENTION

Figure 1A:
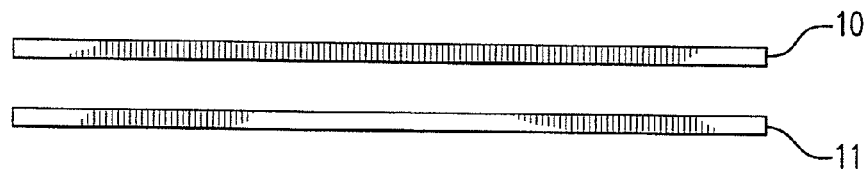
FIG. 1 depicts laminate sheets of extracellular matrix forming a laminate extracellular matrix article.
Figure 1B:
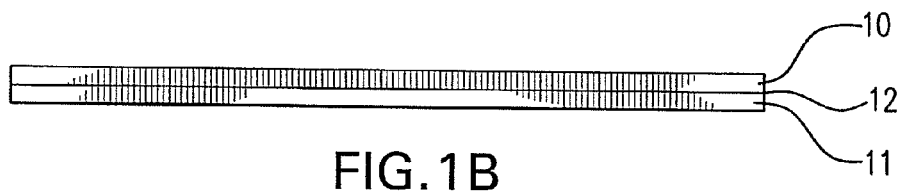
Figure 1C:
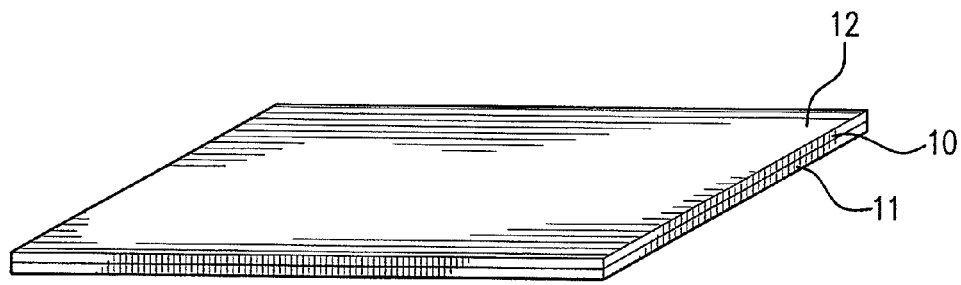
Figure 1D:
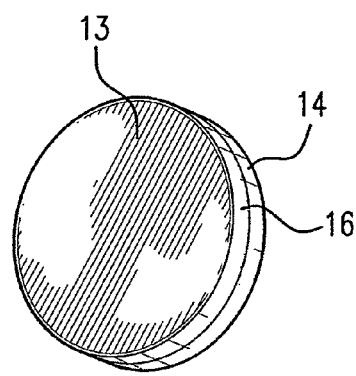
Figure 1E:
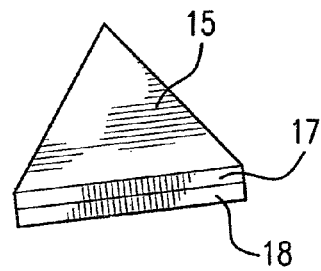

The invention is an article made of extracellular matrix for placing in a mammal at a site in need of tissue regeneration or wound healing to cause tissue regeneration and wound healing. These articles are made from extracellular matrices that are derived from one or more than one tissue source in one or more donor mammals.

The article is a laminate of two or more sheets of extracellular matrix. Accordingly, two components of such an article are first and second sheets of extracellular matrix, that are laminated together to form a laminate of extracellular matrix sheets. The two sheets in this example can be from the same source of extracellular matrix, i.e. both or all from SIS from a pig. The sheets can also be from different tissue sources of extracellular matrix, for example the first sheet is SIS, and the second sheet is SS. Both the SIS and SS can be from the same species of mammal (e.g. pig) or each from a different species of mammal (SIS from pig, and SS from cow). If there are 3 sheets in the laminate article all 3 can be SIS, or the first sheet can be SIS, the second SS, and the third sheet can be SIS, for example. These three sheets can be from the same species of mammal, i.e. a pig, or different mammalian species, i.e. the SIS sheets can be from a pig and the SS sheet can be from a cow.

Advantages are to be derived from using sheets of extracellular matrix from different mammalian tissues, where, for example, each tissue source provides certain attributes. For example, SIS provides tensile strength and the kind of support to newly forming tissue that one would attribute to small intestine submucosa. Adding a sheet from a different tissue, for example one without the tensile strength, but with other regenerative attributes, for example liver basement membrane (LBM), can lend to the article that is a laminate of sheets, an advantageous quality, particularly when two such sheets are laminate together. A sandwich configuration of such sheets can be formed, for example with two outer sheets having relatively substantial tensile strength and an inner sheet of something less strong having other attributes, such as LBM. A SIS-LBM-SIS sheet sandwich may provide the appropriate matrix for tissue regeneration for certain tissues in the body having certain requirements both for strength and regenerative potential.

The article can be two sheets of extracellular matrix encasing a composition. The composition can be any dispersible composition comprising a cell or cells that can rest upon a sheet of extracellular matrix and be covered (and encased by) another sheet. The composition can comprise a cell or cells, such as for example a plurality of stem cells that can aide and promulgate tissue regeneration from the article after placement in the patient. So then, for example the sheets can be SIS and the composition can comprise LBM, or the sheets can be SIS and the gel composition can also be SIS.

For any of these articles, the sheets can be laminated to each other at the edges around an amount of composition (comprising for example cells and other components) that then becomes encased in the two sheets upon lamination of the outer sheets to each other. The lamination of the two outer sheets together can be partial or complete, so that the composition can be entirely contained within the two sheets, or can be permitted to ooze out from between the sheets upon placement in the subject receiving treatment. The composition comprising the cells can also be a composition that supports the cells and allows them to survive and differentiate in that environment.

In another embodiment the sheets can encase one or more cells. The cell or cells can be stem cells. The sheet sandwich can act as support for the growth and development of the cells once placed in the body. The cell or cells can advantageously work in the article to regenerate tissue, or heal damaged tissue in conjunction with the extracellular matrix sheets. The cell or cells can be part of a composition comprising such cells, such as cell media or other material that will help promote the cell survival and differentiation.

The cell in the composition can be any cell, such as, for example a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, a myofibroblast, an osteoblast, a chondrocyte, an exogenous cell, an endogenous cell, a stem cell, a hematopoetic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell. This list is not intended to be exhaustive.

The composition comprising a cell or cells can comprise any material supportive of the purposes of the article and cell culture, cell survival and differentiation. Thus, for example, the composition can comprise extracellular matrix that supports cells in culture and in vivo. The composition can comprise any material supportive of the purposes of the composition and the article in general, such as for example tissue regeneration, wound healing, cell culturing and survival, cell differentiation, stem cell recruitment and the like.

Any composition to support the cells such as an extracellular matrix composition can comprise such forms of extracellular matrix as an emulsion, gel, liquid, paste or particulate placed in between the sheets of matrix can be of mixed source of extracellular matrix, so that for example the gel can be a 50:50 mixture of LBM and UBS. The composition can also be a mixture of LBM and UBS. Thus, the composition can be some mixture or ratio of extracellular matrix from one or more tissue sources.

Generally, for any of the articles of the invention, the components such as sheets of extracellular matrix can be from the same mammalian tissue source (e.g. SIS) or they can be from different tissue sources (e.g. a SIS sheet and an LBM emulsion). Mammalian tissue sources are in general any tissue having an extracellular matrix that can be isolated from a mammal and decellularized. Thus for example, most mammalian organs are tissue sources. The tissue sources can be for example any mammalian tissue, including but not limited to the small intestine, large intestine, stomach, lung, liver, kidney, pancreas, placenta, heart, bladder, prostate, tissue surrounding growing tooth enamel, tissue surrounding growing bone, and any fetal tissue from any mammalian organ.

The forms of the extracellular matrices that make up the articles are generally sheets, although the sheets can be in any shape or size necessary for the site. Thus, for example the sheets can be square, rectangular, triangular, or circular. The sheets can be large or small, depending once again on the site that the article is to be placed.

Placement of the articles in the patients can be accomplished by any reasonable means, including simply placing the article at the site of defect, or attaching the article in place, e.g. by glue or suture.

Extracellular matrix can be obtained from the tissues of mammals by processes such as described in U.S. Pat. Nos. 5,554,389, 4,902,508, and 5,281,422. For example, the urinary bladder submucosa is an extracellular matrix that has the tunica mucosa (which includes the transitional epithelial layer and the tunica propria), a submucosal layer, 3 layers of muscularis, and the adventitia (a loose connective tissue layer). This general configuration is true also for small intestine submucosa (SIS) and stomach submucosa (SS). Obtaining enamel matrices is described in U.S. Pat. No. 7,033,611. Enamel matrix is extracellular matrix existing near forming teeth.

Other tissues such as the liver and pancreas have a basement membrane that does not demonstrate the kind of tensile strength of the tissues defined as submucosa. However, other useful properties may be opportunistically employed from the extracellular matrices of such tissues as the liver, pancreas, placenta and lung tissues which have either basement membrane for extracellular matrix or interstitial membrane (as with the lung). These softer matrices support cells such as those in the organs from which the matrices are derived. Thus, certain benefits are to be found in using the extracellular matrices of these tissues, especially in combination with other such matrices like SIS and SS that may be stronger and which offer their particular advantages. The extracellular matrices surrounding developing tooth enamel and developing bone also have particular advantages over other matrices in that they support the growth and differentiation of the hard tissues of bone and enamel.

Matrices can be used in whole or in part, so that for example, an extracellular matrix can contain just the basement membrane (or transitional epithelial layer) with the sub-adjacent tunica propria, the tunica submucosa, tunica muscularis, and tunica serosa. The matrix composition can contain any or all of these layers, and thus could conceivably contain only the basement membrane portion, excluding the submucosa. However, generally, and especially since the submucosa is thought to contain and support the active growth factors and other proteins necessary for in vivo tissue regeneration, the matrix composition from any given source will contain the active extracellular matrix portions that support cell development and differentiation and tissue regeneration. Thus it is generally understood by persons of skill in the art that the extracellular matrix of any of the mammalian tissue consists of several basically inseparable layers broadly termed extracellular matrix. Where layers can be separated these separate layers can electively be included in the composition, depending on whether they serve the purpose that is the goal of the article being made.

The sheets can come from one or more sources of mammalian extracellular matrix. Thus, for example, the composition can comprise extracellular matrix combinations from such sources as, for example but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart extracellular matrix, dermal matrix, and in general extracellular matrix from any mammalian fetal tissue. Generally a given sheet will be of one source of extracellular matrix, but if the article has two sheets, one sheet can be from one tissue source, and the second sheet can be from a second, different, tissue source.

The compositions of the invention can be made as follows: cells are selected for seeding and placing in between the sheets of extracellular matrix. The cell media is selected and the cells cultured to viability and then placed in the article.

In making the laminates, the ends of the sheets can be sealed using any reasonable means to do so, such as for example gluing or suturing the sheets to each other to form the article. If the sheets are encasing a composition comprising a cell or cells, the sheets are laminated at the outside edges and will encase the cells or cell composition. If a single sheet is folded over to encase a composition, lamination occurs on three sides of the sheet. If a rectangular, or other-shaped article is constructed from two or more sheets in a laminate, lamination occurs at the edges of the article to seal the composition inside, or to affix the sheets together.

For example, sheets can be laminated or layered with each other, so that a sheet of SIS can be placed with a sheet of SS, either with two sheets together SIS-SS or as a sandwich with three sheets, for example SIS-SS-SIS. Also, a different sandwich configuration can be made with two sheets of SIS or SS, sandwiching a gelatinous semi-solid or a solid powder (particulate) form of the matrix. The sandwich can be closed so that a composition can be placed securely between the two outer sheets. A single sheet can alternatively be folded over to encase an amount of composition.

Turning now to the figures, FIG. 1 depicts the laminate sheets in a rectangle shape, and circular and triangle shapes. FIG. 1A depicts a first rectangular sheet 10, and second rectangular sheet 11, before lamination. FIG. 1B depicts rectangular sheet 10 and rectangular sheet 11 laminated together to form laminated article 12. FIG. 1C depicts laminated article 12, having sheets 10 and 11 laminated together in a 3-dimensional perspective to form rectangular laminated article 12. FIG. 1D depicts circular laminated article 13 having laminated circular sheets 14 and 16 laminated together. FIG. 1E depicts laminated article 15 having a triangular shape, formed by lamination of triangular sheets 17 and 18 being laminated together.

Figure 2A:
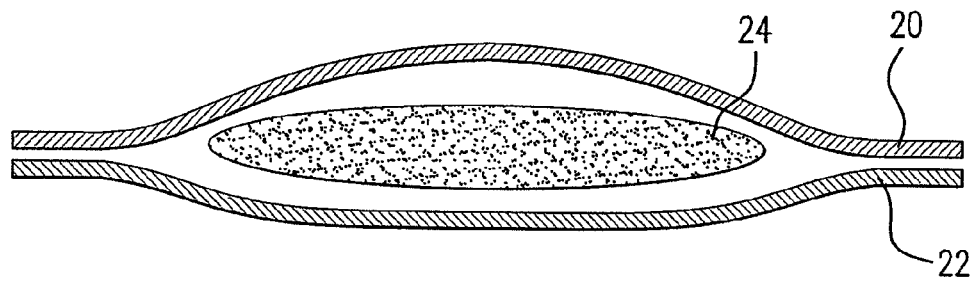
FIG. 2 depicts an article having two sheets of extracellular matrix encasing a composition comprising a cell or a plurality of cells.
Figure 2B:
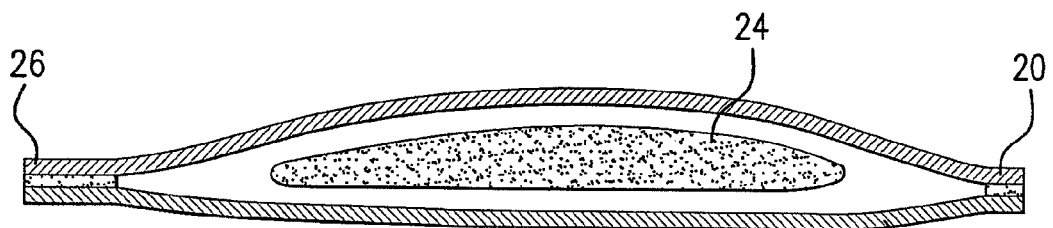
Figure 2C:
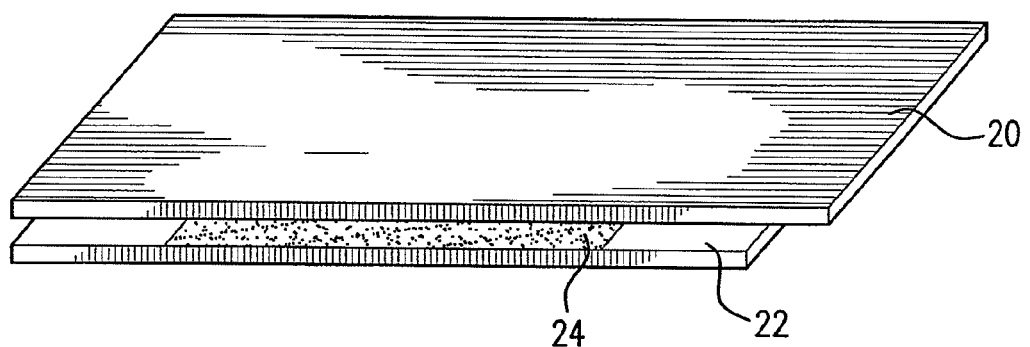
Figure 2D:
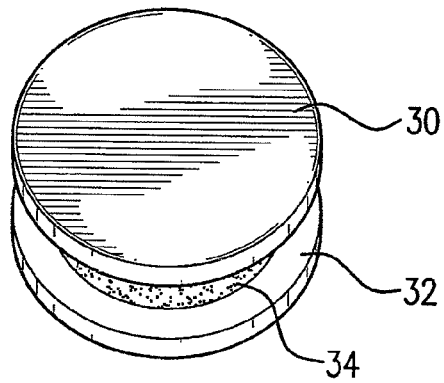

FIG. 2A depicts two sheets, a top sheet 20 and a bottom sheet 22, overlaying a composition 24 comprising cells. FIG. 2B depicts a cross sectional view of the top sheet 20 and bottom sheet 22 laminated at point 26 to encase composition 24. FIG. 2C depicts a 3-dimensional view of top sheet 20 and bottom sheet 22 with composition 24 in between the two sheets, ready for lamination. FIG. 2D depicts a circular article having top sheet 30 and bottom sheet 32 with composition 34 in between them, ready for lamination to close the edges and prepare the article for insertion into a mammalian patient.

Figure 3A:
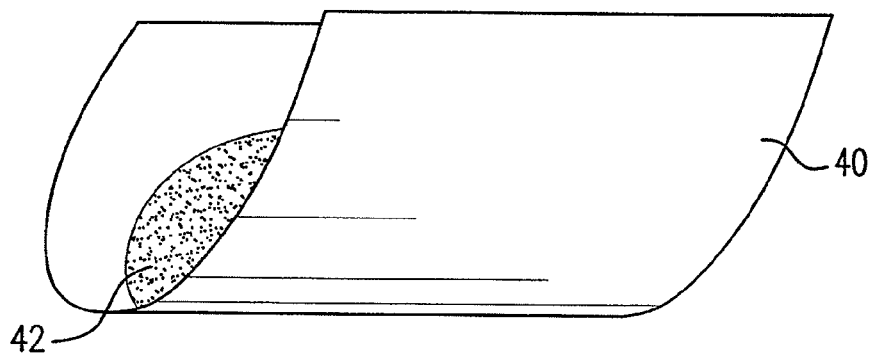
FIG. 3 depicts an article having a single sheet of extracellular matrix that is folded over a composition comprising a cell or a plurality of cells.
Figure 3B:
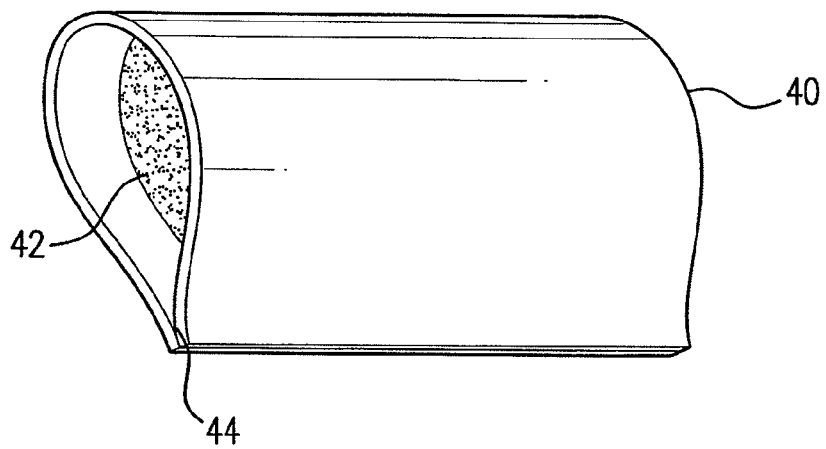
Figure 3C:
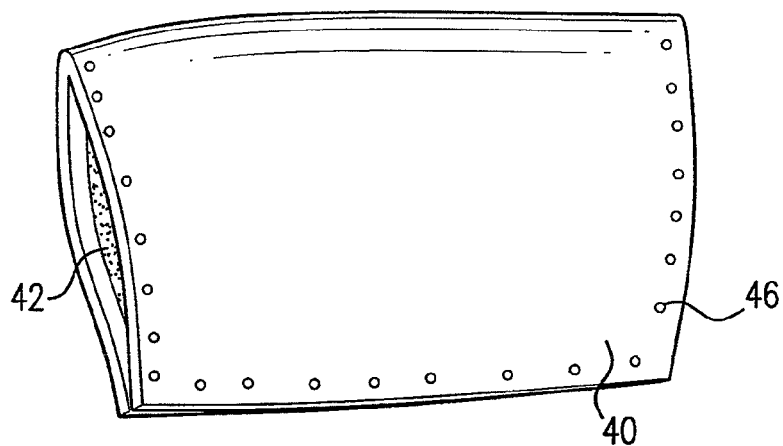

FIG. 3A depicts single sheet 40 encasing composition 42. FIG. 3B depicts single sheet 40 encasing composition 42 having laminated edge 44. FIG. 3C depicts single sheet 40 having composition 42 with laminate points 46 on 3 sides of the article.

The laminate article can encase a composition. The composition can comprise a cell or a plurality of cells. The composition can comprise a stem cell or a plurality of stem cells. The composition can be a material that supports the culturing of the cells. The composition can comprise extracellular matrix in gel or emulsion form that supports cell growth and survival.

The composition that might be encased in one or two sheets of extracellular matrix in addition to comprising a cell or cells might further comprise an additional component. The additional component can be any component that some how serves the composition and its purpose in the mammalian body. Thus, the additional component can help to regenerate tissue, heal a wound, better cultivate cells in the composition, better recruit endogenous stem cells once in the body, manipulate the immune environment in a beneficial way, therapeutically treat the local environment, or otherwise contribute to some aspect of the process for which the composition and article that includes the composition is being used.

Thus, the additional component can be a protein or a drug.

The protein can be for example a growth factor, or any other type or protein that might stimulate some part of the tissue regenerative process. a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD-44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF). This list is not intended to be exhaustive.

The additional component can also be a drug, such as an agent that has therapeutic properties. The drug can be bioactive and play some role in the process of tissue regeneration or act as an antibiotic, antiviral, or other active therapeutic agent serving a purpose in the composition as a whole. The drug can be a small molecule, or any other agent having therapeutic properties.

The invention contemplates using the articles of the invention for contacting a defect in mammalian tissue. The defect can be a cut, disease, wound, burn, scar, necrosis, or other abnormality that would be beneficial to treat. Regenerating tissue at the defect can be one response elicited from the step of placing the extracellular matrix composition in contact with the defect. If the defect is a wound in need of healing, wound healing may be another response that occurs as a result of placing the extracellular matrix at the wound site. In general any term that identifies that the tissue could benefit from a healing or tissue regeneration fits within the scope of the use for the composition. Thus regenerating tissue, or healing a wound are two but the not the only phrases that can be used to describe the effects achieved when the composition is placed in the mammal at a site of defect or damage in tissue.

Therapeutically effective amount is a term meant to capture the idea that you need to apply enough of the composition in sufficient strength so that the composition can have a positive effect on the tissue that is being treated in the subject. The amount may therefore apply to an amount of cell or cells in the composition encased by the laminate. That the amount is therapeutically effective is determined by the composition's ability to have an effect on the regenerative or wound healing activity provided by the article (that encases the composition) as a whole at the site where the article (and composition) contacts the tissue. A therapeutically effective amount is determinable by routine testing in patients with wounds or defects. In general a minimal therapeutically effective amount would be considered sufficient cells (or sufficient amount of an additional component) in the composition to effect the wound healing or tissue regeneration at the site of placement of the article that contains the cells or the additional component.

Regenerating tissue, as is accomplished by placing an article of the invention in a mammal in need of tissue regeneration, is the ability to make tissue regrow, an organ regrow itself, and for tissue to reform or new tissue to form without scarring. Healing a wound is the ability of the tissue to heal preferably without scarring or with very minimal scarring.

All references cited are incorporated in their entirety. Although the foregoing invention has been described in detail for purposes of clarity of understanding, it will be obvious that certain modifications may be practiced within the scope of the appended claims.

What is claimed is:

1. An article for wound healing and tissue regeneration, comprising:
    a first sheet comprising a first mammalian extracellular matrix and a second sheet comprising a second mammalian extracellular matrix, said first and second extracellular matrices comprising small intestine submucosa, said first extracellular matrix sheet having a first outer edge, said second extracellular matrix sheet having a second outer edge, said first and second extracellular matrix sheets being laminated to each other proximate said first and second edges to form a laminated article having a cavity therein, said article further comprising an extracellular matrix composition comprising a third extracellular matrix comprising liver basement membrane, a fourth extracellular matrix comprising urinary bladder submucosa, a cell comprising a mesenchymal stem cell and a protein comprising a growth factor, said growth factor comprising fibroblast growth factor-2 (FGF-2) vascular epithelial growth factor (VEGF), and said extracellular matrix composition being disposed in said article cavity.

2. The article of claim 1, wherein said growth factor comprises a vascular epithelial growth factor (VEGF).

3. An article for wound healing and tissue regeneration, comprising:
    a first sheet comprising a first mammalian extracellular matrix and a second sheet comprising a second mammalian extracellular matrix, said first and second extracellular matrices comprising small intestine submucosa, said first extracellular matrix sheet having a first outer edge, said second extracellular matrix sheet having a second outer edge, said first and second extracellular matrix sheets being laminated to each other proximate said first and second edges to form a planar laminated article having a cavity therein, said article further comprising an extracellular matrix composition comprising a third extracellular matrix comprising liver basement membrane, a fourth extracellular matrix comprising urinary bladder submucosa, a cell comprising a pluripotent cell and a protein comprising a growth factor, said growth factor comprising fibroblast growth factor-2 (FGF-2) vascular epithelial growth factor (VEGF), and said extracellular matrix composition being disposed in said article cavity.

4. The article of claim 3, wherein said growth factor comprises a vascular epithelial growth factor (VEGF).

* * * * *